United States Patent [19]

Shiber

[11] Patent Number: 5,653,696
[45] Date of Patent: Aug. 5, 1997

[54] STENT UNCLOGGING METHOD

[75] Inventor: Samuel Shiber, Atkinson, N.H.

[73] Assignee: Surgical Systems & Instruments, Inc., Manchester, N.H.

[21] Appl. No.: 516,772

[22] Filed: Aug. 18, 1995

Related U.S. Application Data

[63] Continuation-in-part of Ser. No. 107,453, Aug. 17, 1993, Pat. No. 5,443,443, which is a continuation-in-part of Ser. No. 913,231, Jul. 14, 1992, Pat. No. 5,334,211, which is a continuation-in-part of Ser. No. 662,558, Feb. 28, 1991, Pat. No. 5,306,244, which is a continuation-in-part of Ser. No. 499,726, Mar. 27, 1990, Pat. No. 5,135,531, which is a continuation-in-part of Ser. No. 350,020, May 12, 1989, Pat. No. 4,979,939, which is a continuation-in-part of Ser. No. 326,967, Mar. 22, 1989, Pat. No. 4,957,482, Ser. No. 324,616, Mar. 16, 1989, Pat. No. 5,007,896, Ser. No. 323,328, Mar. 13, 1989, Pat. No. 5,002,553, and Ser. No. 332,497, Apr. 3, 1989, Pat. No. 5,024,651, said Ser. No. 326,967, Ser. No. 324,616, Ser. No. 323,328, and Ser. No. 332,497, each is a continuation-in-part of Ser. No.286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 225,880, Jul. 29, 1988, Pat. No. 4,842,579, Ser. No. 205,479, Jun. 13, 1988, Pat. No. 4,883,458, and Ser. No. 78,042, Jul. 27, 1987, Pat. No. 4,819,634, said Ser. No. 225,880, Ser. No. 205,479, and Ser. No. 78,042, each is a continuation-in-part of Ser. No.18,083, Feb. 24, 1987, Pat. No. 5,041,082, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^6$ ............................................. A61M 25/00
[52] U.S. Cl. ................................. 604/267; 604/280
[58] Field of Search ............................ 604/22, 266, 267, 604/280; 606/108, 159, 167, 170, 171, 180; 128/772

[56] References Cited

U.S. PATENT DOCUMENTS

| | | | |
|---|---|---|---|
| 4,979,939 | 12/1990 | Shiber | 606/159 |
| 5,047,040 | 9/1991 | Simpson et al. | 606/159 |
| 5,078,723 | 1/1992 | Dance et al. | 606/159 |

*Primary Examiner*—Corrine M. McDermott
*Attorney, Agent, or Firm*—Samuel Shiber

[57] ABSTRACT

A process and apparatus for removing obstruction material from a stent which is located in a vessel in a body. The process generally involves threading a flexible casing into the material, and optionally, passing a tubular blade over the material to separate the material from the stent, and then withdrawing the flexible casing and the material out of the stent.

5 Claims, 7 Drawing Sheets

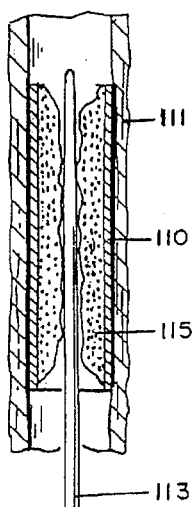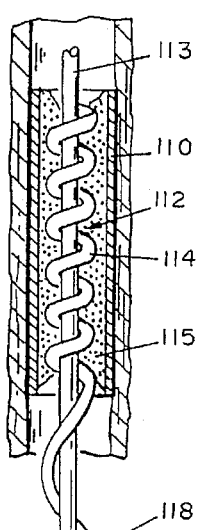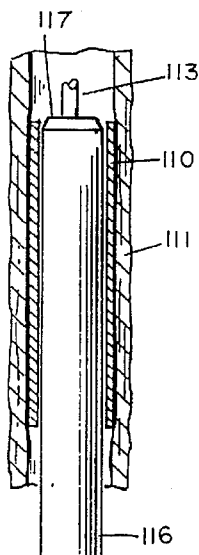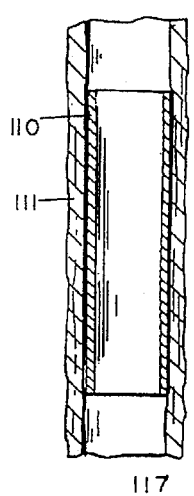
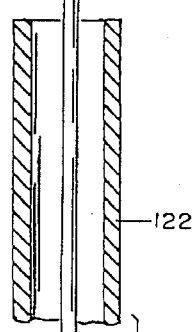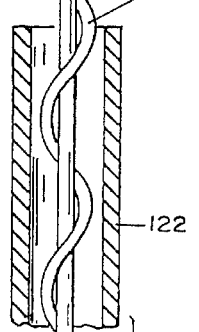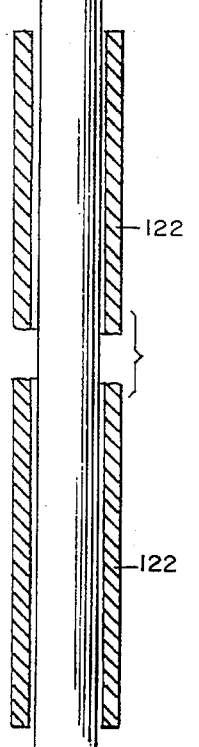
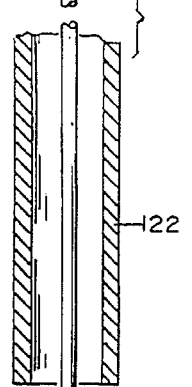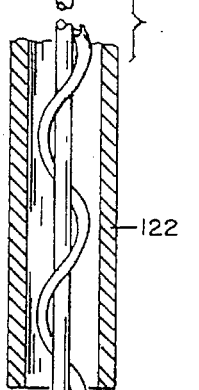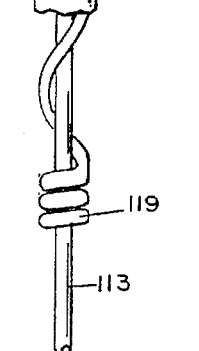
FIG. 31
FIG. 28  FIG. 29  FIG. 30

STENT UNCLOGGING METHOD

CROSS REFERENCE TO OTHER APPLICATIONS

This application is a continuation in part (CIP) of appl. Ser. No. 08/107,453 filed Aug. 17, 1993 now U.S. Pat. No. 5,443,443 which is a CIP of appl. Ser. No. 07/913,231 filed Jul. 14, 1992 now U.S. Pat. No. 5,334,211 which is a CIP of appl. Ser. No. 07/662,558 filed Feb. 28, 1991 now U.S. Pat. No. 5,306,244 which is a CIP of appl. Ser. No. 07/499,726 filed Mar. 27, 1990 now U.S. Pat. No. 5,135,531 which is a CIP of appl. Ser. No. 07/350,020 filed May 12, 1989 now U.S. Pat. No. 4,979,939 which is a CIP of four applications: Appl. Ser. No. 07/326,967 filed Mar. 22, 1989 now U.S. Pat. No. 4,957,482, appl. Ser. No. 07/324,616 filed Mar. 16, 1989 now U.S. Pat. No. 5,007,896, appl. Ser. No. 07/323,328 filed Mar. 13, 1989 now U.S. Pat. No. 5,002,553 and appl. Ser. No. 07/332,497 filed Apr. 3, 1989 now U.S. Pat. No. 5,024,651.

These four applications are CIPs of appl. Ser. No. 07/286,509 filed Dec. 19, 1988 now U.S. Pat. No. 4,894,051 which is a CIP of appl. Ser. No. 07/243,900 filed Sep. 13, 1988 now U.S. Pat. No. 4,886,490, which is a CIP of three applications:

Appl. Ser. No. 07/225,880 filed Jul. 29, 1988 now U.S. Pat. No. 4,842,579, appl. Ser. No. 07/205,479 filed Jun. 13, 1988 now U.S. Pat. No. 4,883,458, and appl. Ser. No. 07/078,042 filed Jul. 27, 1987 now U.S. Pat. No. 4,819,634. These three applications are CIPs of appl. Ser. No. 07/018,083 filed Feb. 24, 1987 now U.S. Pat. No. 5,041,082 which is a CIP of appl. Ser. No. 06/874,546 filed Jun. 16, 1986 now U.S. Pat. No. 4,732,154 which is a CIP of appl. Ser. No. 06/609,846 filed May 14, 1984 now abandoned.

All the above applications are being incorporated herein by reference.

BACKGROUND AND OBJECTIVES OF THE INVENTION

With age, a large percentage of the population develops atherosclerotic arterial obstructions resulting in diminished blood circulation. The disturbance to the blood flow that these obstructions cause may induce blood clots which further diminish or block the blood flow. When this process occurs in the coronary arteries it is referred to as a "heart attack". Presently such obstructions are circumvented surgically by grafting a bypass or they are treated by a catheter equipped with a balloon which is inserted through the arterial system, over a flexible guide wire assembly, into the obstruction and then inflated to expand the obstruction's lumen, a procedure known as angioplasty.

Angioplasty, which breaks up but does not remove the obstruction material out of the arterial system, creates an irregular lumen which tends to partially recoil after the balloon is deflated and withdrawn. To lessen this phenomena a stent may be placed in the blood vessel to provide support (further information on intravascular stents is available in chapter 56 of the 2nd edition of a book titled *Endovascular Surgery* by Samuel S. Ahn and Wesley S. Moore, which was published in 1992 by W. B. Saunders Co. which is hereby incorporated by reference).

Stents may also be useful in other vessels of the human anatomy, therefore, the term "vessel" as used hereinafter shall mean a tubular fluid conduit in the body such as blood vessels and biliary ducts. For example, stents may be inserted in narrowed biliary ducts to keep these ducts open for bile drainage (further information on biliary stents is available in chapter 7 of the 3rd edition of a book titled *Practical Gastrointestinal Endoscopy* by Peter B. Cotton and Christopher B., Williams, which was published by Blackwell Scientific Publications which is hereby incorporated by reference).

The stent itself, however, may become obstructed. An objective of the present invention is to provide a stent unclogging method and hardware for reopening and cleaning obstructed stents.

These and other objectives of the invention will become apparent from the following discussion and the accompanying drawings.

BRIEF DESCRIPTION OF THE FIGURES

FIG. 1' generally shows a stent unclogging system inserted through a patient's digestive system into an obstructed stent in the patient's vessel (biliary duct).

FIG. 7' shows an enlarged, partially sectioned view, of the distal end section of a helical wire where the distal entry to the void defined between the coils, is selectively closed by a thin walled cylinder.

FIGS. 28 to 30 illustrate a variety of processes for unclogging a stent which is located in a patient's vessel.

FIG. 28 depicts a flexible guide wire inserted into an obstruction which clogs the stent.

FIG. 29 depicts a flexible guide wire and flexible casing inserted into an obstruction which clogs the stent.

FIG. 30 depicts a flexible guide wire, flexible casing, and flexible rotary catheter passed through a stent.

FIG. 31 shows the desired result, in the form of a stent with an open passage for fluid flow.

DETAILED DESCRIPTION OF THE DRAWINGS

Figure 1:
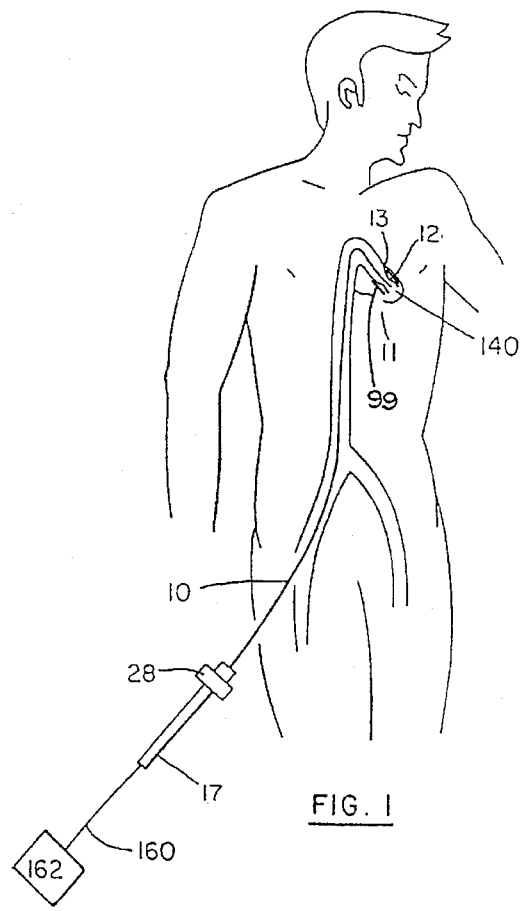
FIG. 1 generally shows a stent unclogging system inserted at the groin area through the arterial system of a patient, into an obstructed stent into a vessel (coronary artery).
Figure 1:
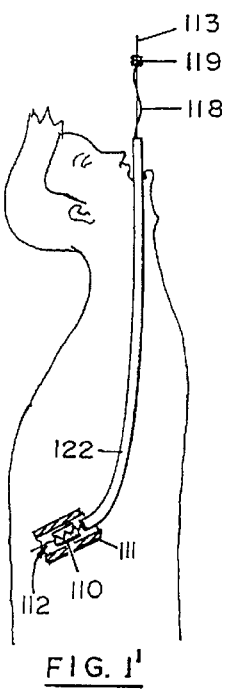

FIG. 1 generally shows a stent unclogging system 10 (similar parts will be indicated by the same numbers throughout the FIGURES) inserted at the groin area through the skin, through a patient's vascular system into an obstructed stent 99 located within a vessel (artery) 13 serving the patient's heart 11.

FIG. 1' generally shows a stent unclogging system inserted through a patient's mouth, throat, and into the digestive system where it is inserted, through an endoscope 122, into an obstructed stent 110 in a patient's vessel (biliary duct) 111.

Figure 2:
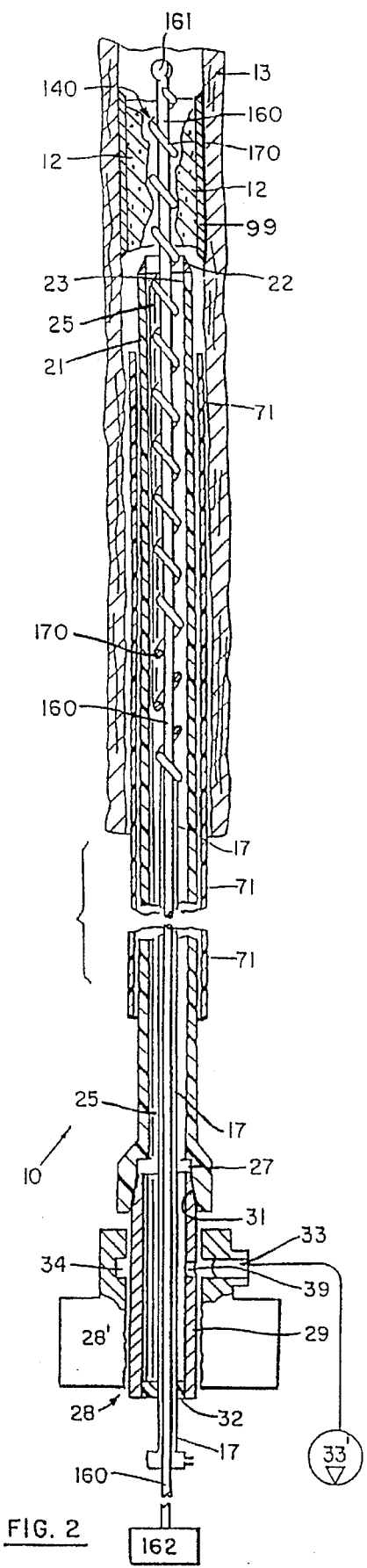
FIG. 2 shows a cross sectioned view of a stent unclogging system with a flexible guide wire assembly having a flexible casing in the form of a helical wire surrounding a flexible guide wire which incorporates an ultrasound transducer.

FIG. 2 shows a stent unclogging system 10 for removing an obstruction 12 from within an obstructed stent 99 in a patient's vessel (artery) 13. The stent unclogging system comprises several elongated parts in a nested relationship, and their ends shall be referred to as "distal" meaning the end which goes into the vessel and "proximal" meaning the end portion which remains outside the vessel. Thus, "distal direction" or "distally" shall indicate a general direction from the proximal end to the distal end, and "proximal direction" or "proximally" shall refer to an opposite direction.

Figure 6:
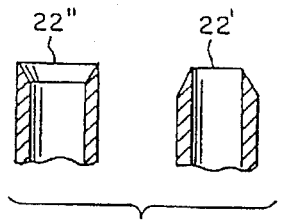
FIG. 6 shows optional tubular blade designs.

The stent unclogging system illustrated in FIG. 2 comprises:

A flexible guide wire assembly 140 insertable into the vessel. A flexible rotary catheter 21 slidable over the flexible guide wire assembly, The flexible rotary catheter has a tubular blade 22 at its distal end for separating the obstruction from the stent and it defines a continuous passage 25 around the flexible guide wire assembly for ingesting the cut obstruction material. As shown in FIG. 6, in an enlarged cross sectional view, the preferred design of tubular blade 22 has a cutting edge sharpened along its internal diameter as illustrated by 22'. FIG. 6 also shows an optional design for the tubular blade 22 which has a cutting edge sharpened along its outside diameter as illustrated by 22". This optional design removes more of the obstruction material but also increases the probability of removing, or nicking, part of the vessel's wait The flexible guide wire assembly may include a thin wall stainless steel tube 17 which may be attached to a flexible casing, preferably a helical wire illustrated by 170. Furthermore, the helical wire is preferably auger shaped. Optionally, the flexible casing is slidable over and guided by a flexible guide wire 160. A helical void is defined between the coils of the helical wire 170 for holding the obstruction material.

When the flexible rotary catheter's distal end 23 bears against the vessel's wall the contact force is spread on a relatively large area and the damage to the vessel's wall is minimized.

Suction can be applied to the flexible rotary catheter through a port 33 which communicates with a groove 34 defined by the motor's housing, which communicates with hole 39, which communicates with the hollow shaft 29 which communicates with the proximal end of the continuous passage 25. Suction is provided by suction means 33'. Preferably, the suction is provided by a positive displacement pump such as a piston pump or a peristalic pump which tends to self regulate the evacuation process, limiting the amount of blood removed through the flexible rotary catheter to the volume that is positively displaced by the pump. When only free flowing blood is present in the continuous passage, the negative pressure in the continuous passage drops. As obstruction material enters the continuous passage the negative pressure rises and pulls the cut material proximally (the level of negative pressure can be limited by an internal relief valve in the pump). The suction can be synchronized with the rotation of the tubular blade, or it can be otherwise selectively controlled to further minimize blood evacuation. The suction cooperates with mechanical agitation in transporting the obstruction material through the flexible rotary catheter.

Coupling means at the proximal end of the flexible rotary catheter in the form of a conical seat 27 couples it to drive means in the form of a motor having a housing 28 and a hollow shaft 29 with a matching tapered end 31 and a seal 32 at its other end. The hollow shaft and seal are slidingly disposed around the proximal end of the flexible guide wire assembly. The guide wire 160 contains means for transmission of energy between an ultrasound transducer 161 mounted at its distal end and a base unit 162 connected to its proximal end. The base unit sends, through the guide wire, electrical energy to the transducer and receives back a signal which is translated by the base unit to a map of the surrounding obstruction and tissue. The information enables a physician to safely navigate the guide wire through the vessel.

The flexible guide wire assembly 140 does several things: It acts as a barrier which negates the obstruction material's distal movement during the unclogging process. It also restrains the freed obstruction sections from freely rotating around the flexible guide wire assembly, and to the extent that they do rotate, this rotation is used to urge the freed obstruction sections proximally in the continuous passage. In addition, when the flexible guide wire assembly has to be inserted into an obstruction, the helical wire can be threaded into the obstruction by rotating it, causing the helical wire to pull itself into and across the obstruction. Further, the helical wire guides the flexible rotary catheter 21, taking up the free play between the flexible guide wire 160 and the flexible rotary catheter.

Figure 5:
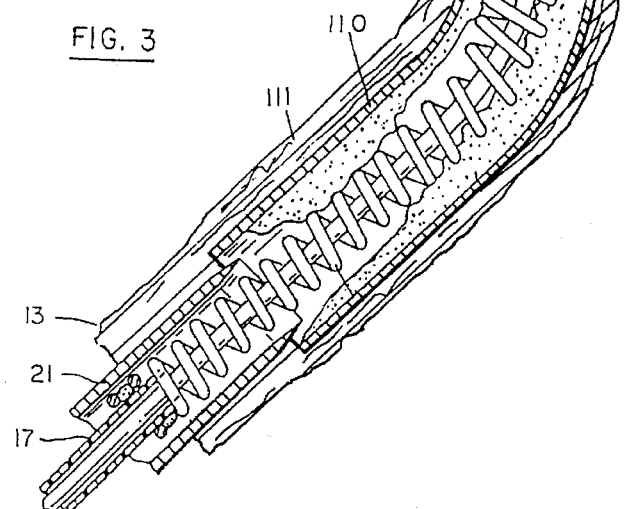
FIG. 5 shows a stent unclogging system opening a cross sectioned, curved stent located in a vessel (biliary duct).

FIG. 5 illustrates how the flexible casing, in the form of the helical wire 170, accurately guides the flexible rotary catheter 21 and the tubular blade to separate the clogging material from the obstructed stent 110 without damaging the wall of the stent or of the vessel (biliary duct) 111.

Referring back to FIG. 2, a flexible sleeve 71 in which the flexible rotary catheter is disposed, protects the vessel's wall from the rotating catheter, and can be used to introduce the flexible rotary catheter into the vessel.

Figure 3:
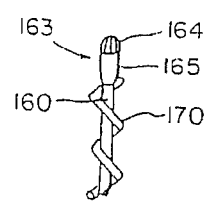
FIG. 3 shows an optional distal end of the ultrasound transducer with protrusions on its distal end.

FIG. 3 shows a modified ultrasound transducer 163 having protrusions 164 on its distal end and having a smooth mid-section 165 for transmitting and receiving ultrasound energy. The protrusions allow a physician to use the transducer as a drill by rotating the guide wire, and thereby enabling it to cross tight or total obstructions with the relative safety of knowing the transducer's position relative to the vessel's wall, via a base unit (such as the base unit 162 in FIG. 2). Alternate non-mechanical energy, for example heat, laser energy or other frequencies of electromagnetic waves, could be used with proper modification of the flexible guide wire 160 to carry such frequencies, and of an ultrasound transducer and base unit to transmit and receive such frequencies. Such energy being sent from the base unit to an ultrasound transducer could also be used to assist the transducer in penetrating through the obstruction, with or without rotation thereof. Optionally, very small protrusions can be attached to the transducer, e.g., diamond particles, to enable the transducer, when it is rotated, to drill through the obstruction.

The ultrasound energy which is emitted by the transducer is partially transmitted to the helical wire 170 and to the adjacent obstruction material to assist the helical wire 170 in threading through the obstruction material.

Figure 4:
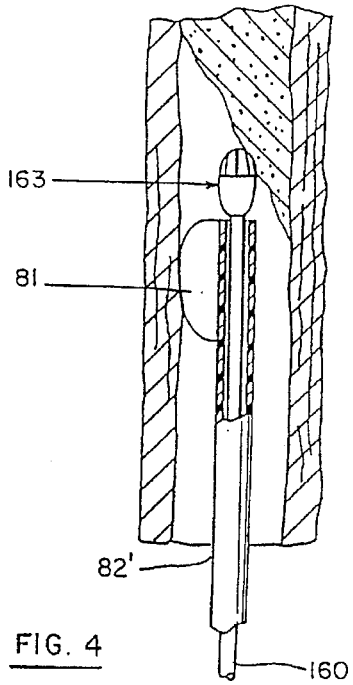
FIG. 4 shows a distal end of a flexible guide wire disposed in a deflecting catheter. The flexible guide wire has an ultrasound transducer mounted at its distal tip. The ultrasound transducer's distal end is equipped with protrusions.

FIG. 4 shows a distal portion of a flexible guide wire 160 disposed in a deflecting sleeve 82' for deflecting the trajectory of the flexible guide wire in the vessel. The deflecting sleeve 82' is a scaled down version of the deflecting sleeve shown in FIGS. 20 and 21 and performs in the same manner. The deflecting sleeve 82' can also guide the whole flexible guide wire assembly through the vessel.

Figure 7:
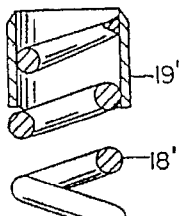
FIG. 7 shows an enlarged, partially sectioned view of the distal end section of a helical wire where the distal entry to the void, which is defined between the coils, is selectively closed by a thin walled cylinder. The term "selectively closed" means that the thin walled cylinder prevents the guide wire from entering the void, but it minimally interferes with the entry of obstruction material into the void. The helical wire is made of a tube through which non-mechanical energy can be conveyed to the distal end to preferably assist in threading the helical wire through an obstruction, in addition to mechanical energy that can be transmitted through the helical wire itself.
Figure 8:
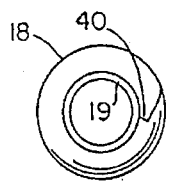

FIG. 7 shows an enlarged, partially sectioned view of the distal end section of a flexible casing in the form of a helical wire 18 where the distal entry to the void which is defined between the coils is selectively closed by a gate in the form of a thin walled cylinder 19 attached to and located inside the flexible casing. The helical wire is made of a tube through which non-mechanical energy, for example laser energy, can be conveyed to the distal end to assist in threading the helical wire through an obstruction in addition to the mechanical energy that can be transmitted through the tube itself.

Figure 8:
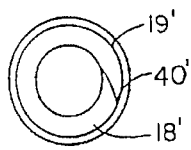
FIG. 8 shows the end view of the helical wire shown in FIG. 7.

FIG. 8 shows the end view of the helical wire shown in FIG. 7, having a sharpened tip 40.

FIG. 7' shows an enlarged, partially sectioned view of the distal end section of a flexible casing in the form of a helical wire 18', where the distal entry to the void which is defined between the coils is selectively closed by a gate in the form of a thin walled cylinder 19' attached to and located outside of the flexible casing.

FIG. 8' shows the end view of the helical wire shown in FIG. 7' having a helical wire 18' with a sharpened tip 40'.

Figure 9:
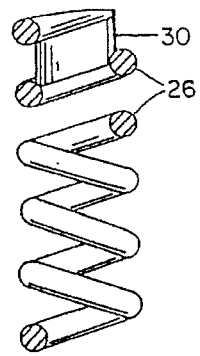
FIG. 9 shows an enlarged, partially sectioned view of the distal end section of a helical wire where the distal entry to the helical void, which is defined between the coils, is selectively closed by a thin walled cylindrical section.

FIG. 9 shows an enlarged, partially sectioned view of the distal end section of a flexible casing in the form of a helical wire 26 where the distal entry to the helical void defined between the coils is selectively closed by a gate in the form of a thin walled cylindrical section 30 which is attached to and is located inside the flexible casing.

Figure 10:
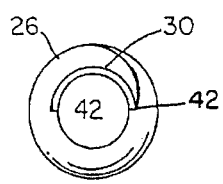
FIG. 10 shows the end view of the helical wire shown in FIG. 9.
Figure 7:
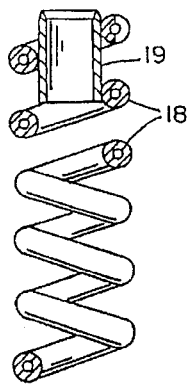

FIG. 10 shows the end view of the helical wire shown in FIG. 9, having a sharpened tip 42.

Figure 12:
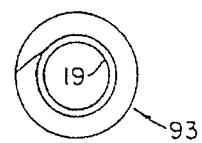
FIG. 12 shows the end view of the helical wire shown in FIG. 11.
Figure 11:
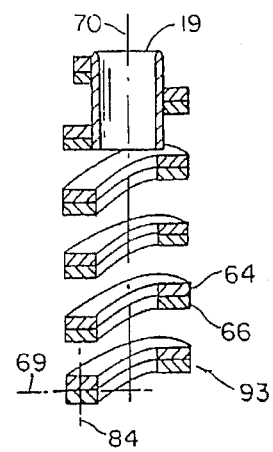
FIG. 11 shows an enlarged, sectioned view of the distal end section of a helical wire made of two flat layers, where the distal entry to the helical void which is defined between the coils, is selectively closed by a thin walled cylinder.

FIGS. 11 and 12 show an enlarged, sectioned view of the distal end section of a helical wire made of two flat layers, where the distal entry to the helical void defined between the coils is selectively closed by a thin walled cylinder which is attached to and is located inside the flexible casing.

FIG. 11 shows an enlarged, sectioned view of the distal end section of a helical wire 93 made of two flat layers 64 and 66, where the distal entry to the helical void defined between the coils is selectively closed by a thin walled cylinder 19. By forming the helical wire 93 from two layers, the cross section modulus of the helical wire 93 around an axis 69, which is perpendicular to the helical wire's axis 84, is decreased (for orientation, helical wire's axis 84 is parallel to the flexible casing axis 70).

FIG. 12 shows the end view of the helical wire shown in FIG. 11.

Figure 13:
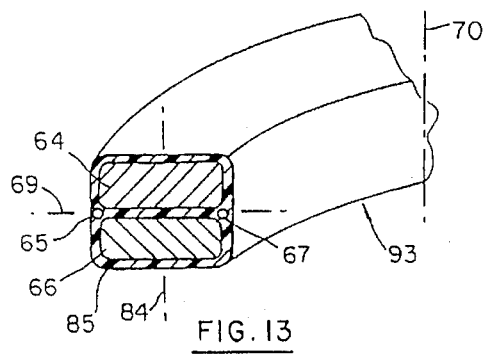
FIG. 13 shows a further enlargement of the cross section of the helical wire of FIG. 11.

FIG. 13 shows a further enlargement of the cross section of the helical wire of FIG. 12. The two flat layers 64 and 66 are encapsulated in a plastic material 85 which holds them together and makes them thread through the obstruction material in unison, as one piece, but is sufficiently flexible to allow their cross section modulus to be that of two separate layers. Non-mechanical energy conduits 65 and 67, for example electrical wires or fiber optical bundles, are also encapsulated by the plastic material. Preferably, the plastic material has a slippery outer surface to ease the casing's insertion through the vessel and threading it through the obstruction material.

Figure 16:
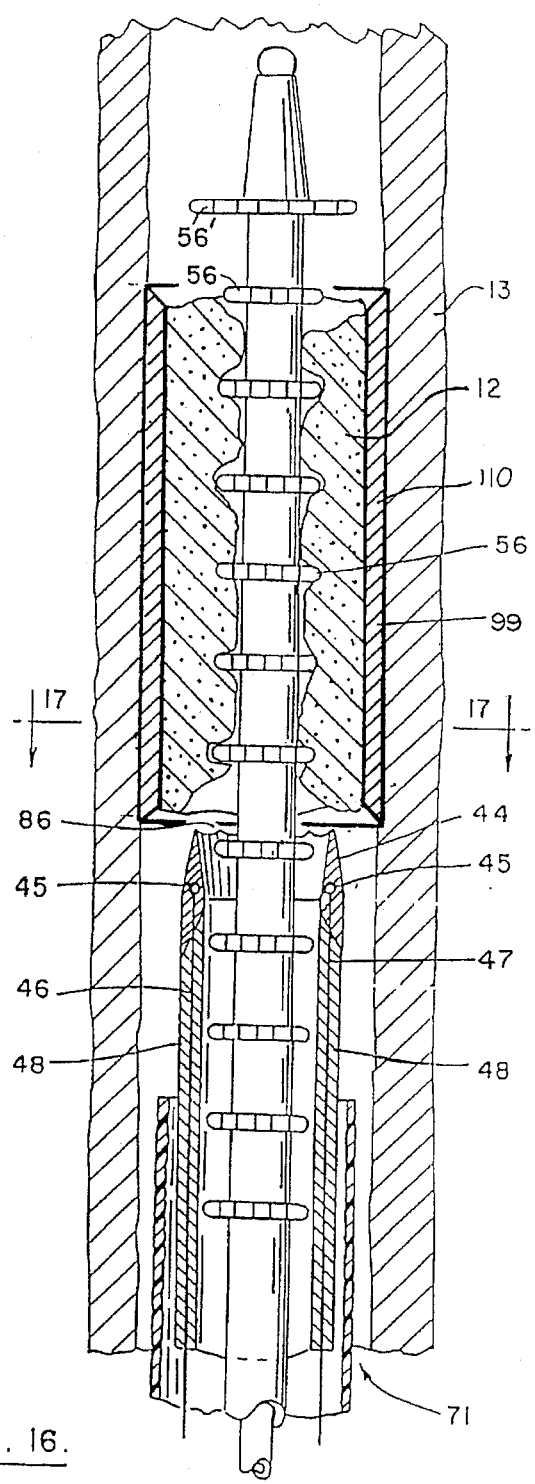
FIG. 16 shows a cross sectioned view of the distal end portion of a stent unclogging system with a tubular-blade, which utilizes auxiliary non-mechanical energy, disposed over a flexible guide wire assembly having barrier means in their expanded position (FIG. 14 shows the barrier means in their closed position).
Figure 14:
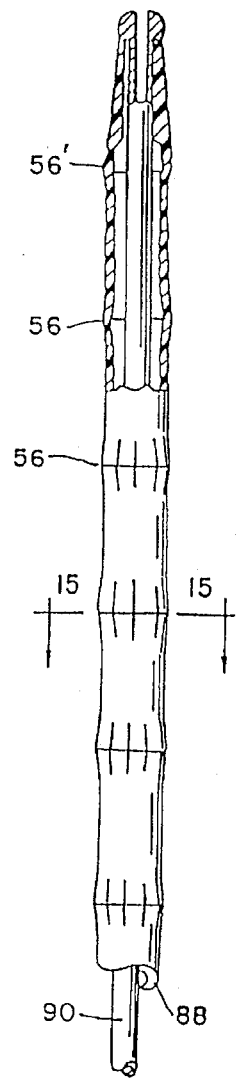
FIG. 14 shows a flexible guide wire assembly with the barrier means in their closed position.

FIG. 14 shows the flexible guide wire assembly shown in FIG. 16 with the barrier elements 56 in their closed position.

The barrier elements can be selectively expanded by holding the proximal end of a wire 90 while pushing the thin plastic jacket 88 forward until the barrier elements 56 fold.

Figure 15:
FIG. 15 shows a cross sectioned view of the system shown in FIG. 14 along a line 15—15 marked on FIG. 14.

FIG. 15 shows a cross sectioned view of the system shown in FIG. 14 along a line 15—15 marked on FIG. 14.

FIG. 16 shows a distal end portion of a stent unclogging system having a tubular blade 44 with teeth 86 and a ring shaped heating element 45 built into the blade, to which non-mechanical energy is brought by means of two flexible conduits 46 and 47 disposed in a wall of a flexible rotary catheter 48. The heating can be done electrically, in which case the flexible conduits 46 and 47 are electrical wires and the heating element can be a resistive element. The heating can also be done with laser energy in which case the flexible conduits 46 and 47 can be optical fibers and the heating element can serve to absorb the laser energy from the distal end of the optical fibers and translate it to heat and distribute it to the tubular blade 44. Optionally, the tubular blade 44 can be made from semi-transparent or transparent material, and part or substantially all of the laser energy can be transmitted, respectively, to the obstruction material. A flexible guide wire assembly has barrier element 56 to counter distal movement of surrounding obstruction material. The barriers can be made of a thin plastic jacket 88 with a series of slits. In their open position the barrier elements 56 form a barrier to prevent the obstruction material from moving distally in the vessel and in the continuous passage while the flexible rotary catheter cuts and ingests the obstruction material. The diameter of the top barrier element 56', when open, can be made larger than the inner diameter of the flexible rotary catheter to block a larger cross sectional area of the vessel whereas the diameter of barrier elements 56, when open, are made to fit inside the flexible rotary catheter which they guide and slidably support.

Since the obstruction material is positively held in voids defined between barrier elements 56 and since the non-mechanical energy delivered to the tubular blade through flexible conduits 46 and 47 eases the coring process, it may be possible to cut softer obstruction material by pushing the catheter without rotating it, especially where there is an anatomical reason not to impart frictional torque onto the vessel. However, rotating the catheter and blade provides more effective cutting and also reduces the linear frictional drag between the catheter and the vessel, and is, therefore, preferable in most cases.

Figure 17:
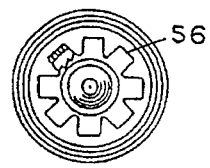
FIG. 17 shows a cross sectioned view of the stent unclogging system assembly shown in FIG. 16 along a line 17—17 marked on FIG. 16.

FIG. 17 shows a cross sectioned view of the flexible guide wire shown in FIG. 16 along a line 17—17 marked on FIG. 16.

Figure 18:
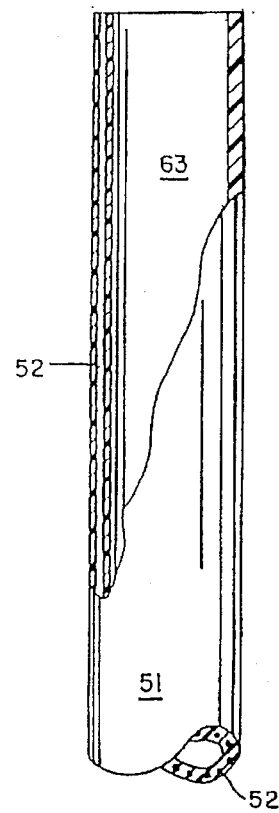
FIG. 18 shows a cross sectioned view of a stent unclogging system having a radiation emitting device used to separate the obstruction from the vessel's wall.

FIG. 18 shows a stent unclogging system having a flexible catheter 51 where separation of the obstruction from the vessel is done with a radiation emitting device through optical fibers 52 which emit laser energy through their distal ends. The radiation energy cuts the obstruction by cutting a narrow channel in it and the continuous passage 63 ingests the cut obstruction material as in previous embodiments. Similarly to the tubular-blade, the embodiment of FIG. 18 separates the obstruction from the vessel's wall and uses less energy in comparison to other laser based systems which pulverize the bulk of the material of the obstruction. The flexible catheter 51 can be rotatably disposed in any of the sleeves shown in connection to the embodiments of the present invention. By using a sleeve equipped with a toroidal chamber to block blood flow and by introducing fluid, saline solution for example, through the sleeve or the flexible catheter, a working medium of choice can be created to suit a specific type of radiation and to allow visual or spectroscopic analysis of the vessel's lumen.

When a plurality of optical fibers 52 are used, as shown in FIG. 18, it may be possible to cut and separate the obstruction from the stent's wall by pushing the flexible catheter 51 distally while slightly rotating it back and forth, which also minimizes the linear frictional torque imparted on the vessel's and stent's wall.

Figure 19:
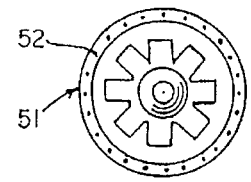
FIG. 19 shows the end view of the system shown in FIG. 18 with the flexible guide wire assembly having barrier means in their expanded position, similar to the guide wire assembly shown in FIG. 17.

FIG. 19 shows a distal end view of the system shown in FIG. 18 with the guide wire assembly that has been incorporated in the embodiment of FIG. 16.

Figure 20:
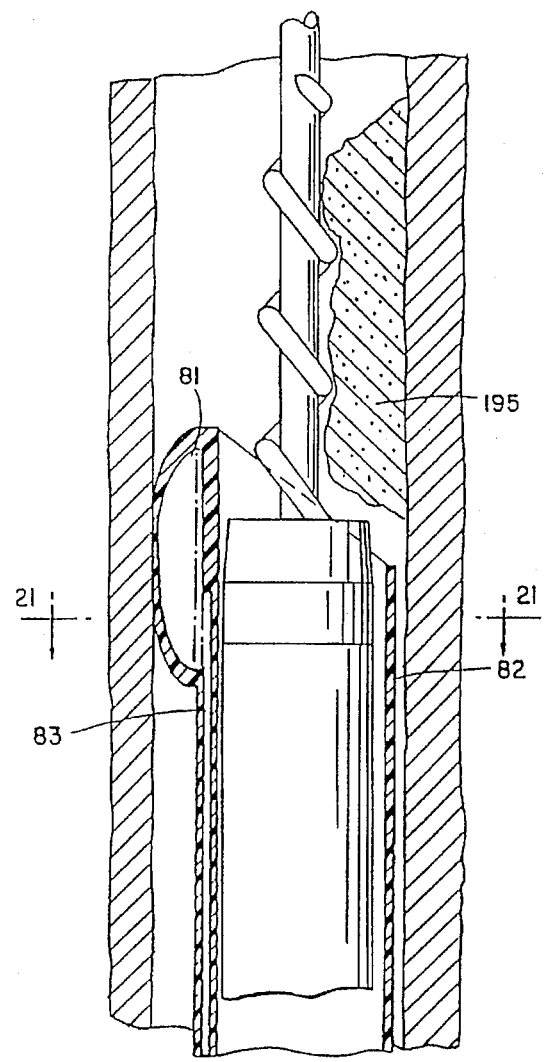
FIG. 20 shows a cross sectioned view of a stent unclogging system with an inflatable chamber located at the distal end of the flexible sleeve in which a flexible rotary catheter is slidably and rotatably disposed.
Figure 21:
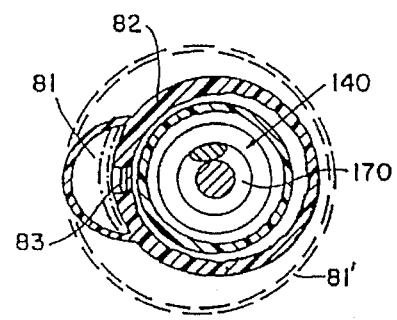
FIG. 21 shows a cross sectioned view of the system shown in FIG. 20 along a line 21—21 marked on FIG. 20.

FIGS. 20 and 21 show a biasing means in the form of an asymmetrical inflatable chamber 81 which is formed at the distal end of a flexible deflecting sleeve 82. When inflated through a channel 83 formed in the sleeve's wall, the chamber bears against the vessel's wall, as shown in solid lines, eccentrically biasing the flexible sleeve and the coring means, When deflated, as shown by phantom lines, the chamber conforms to the sleeve to minimize interference with its insertion into the vessel. Alternatively the chamber can be shaped as an asymmetrical toroidal inflatable chamber 81' as shown in FIG. 21 by interrupted lines. This chamber, when inflated, establishes peripheral contact with the vessel's wall and thereby blocks blood flow between the sleeve and the vessel's wall, as well as eccentrically biasing the sleeve (it can be s understood that a symmetrical toroidal chamber can be provided for the purpose of blocking the flow around the sleeve without eccentrically biasing the sleeve). Any of the above mentioned chambers can also be inserted into the lumen that has been cut by the tubular blade, to be inflated therein and to further widen the lumen, however, such a procedure may have some of the drawbacks of angioplasty.

Figure 22:
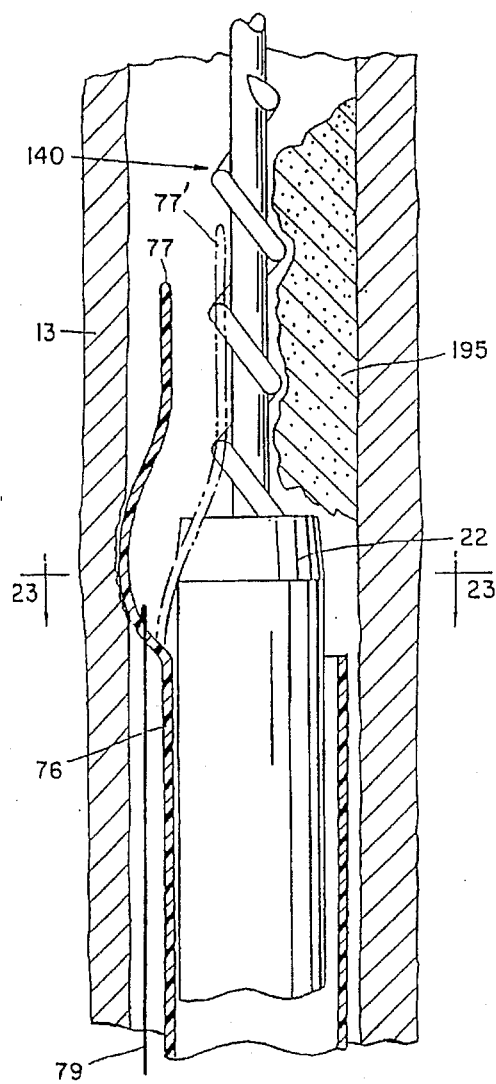
FIG. 22 shows a cross sectioned view of a stent unclogging system with a flexible sleeve having a selectively actuable tongue at its distal end.
Figure 23:
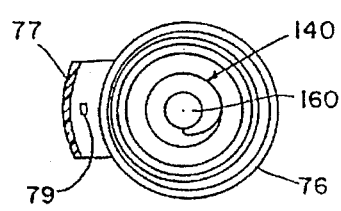
FIG. 23 shows a cross sectioned view of the tongue shown in FIG. 22 along the line 23—23 marked on FIG. 22.

FIGS. 22 and 23 show a stent unclogging system where a flexible sleeve 76 has a tongue 77 which can be used when coring an eccentric obstruction 195. In such a case the tongue can be inserted opposite of the obstruction to protect a vessel's wall (artery) 78 and bias the trajectory of the coring means into the obstruction. The tongue can be energized against the vessel's wall by tensioning a wire 79, moving the tongue from its relaxed position shown by a phantom line in FIG. 22 and marked 77' to the position shown in solid lines and marked 77 (which may ease the insertion of the flexible sleeve 76).

Figure 25:
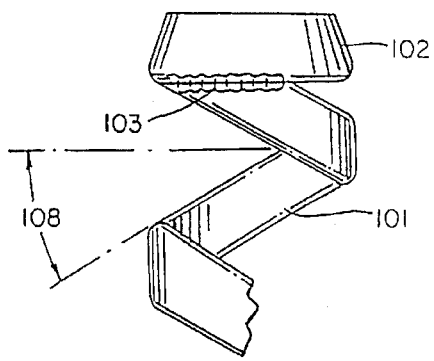
FIG. 25 shows a distal portion of the open coil flat wire spring shown in FIG. 24.
Figure 24:
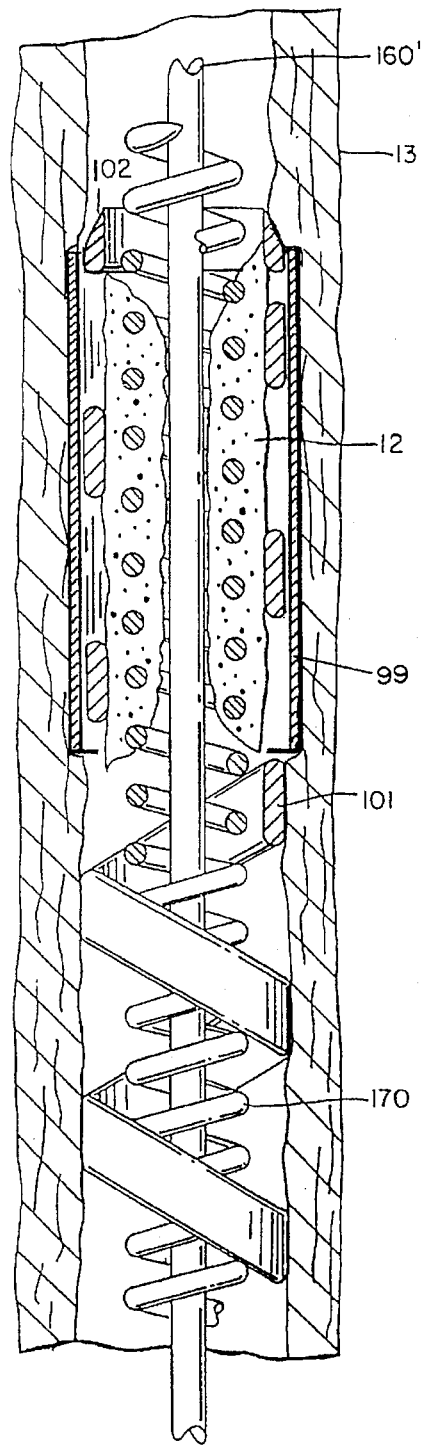
FIG. 24 shows a cross sectioned view of a distal portion of a stent unclogging system with a flexible guide wire assembly having a flexible casing in the form of a helical wire wound around a flexible guide wire, and a flexible rotary catheter in the form of an open coil flat wire spring.

FIG. 24 shows a cross sectioned view of a distal portion of a stent unclogging system with a flexible guide wire assembly having a flexible casing in the form of a helical wire 170 wound around a flexible guide wire 160', and a flexible rotary catheter in the form of an open coil flat wire spring 101 which is attached, at its distal end, to a tubular blade 102. FIG. 25 shows a distal portion of the flexible rotary catheter which is shown in FIG. 24, and the tubular blade 102 which is attached to the open coil flat wire spring 101 by a weld 103. Numeral 108 designates the helix angle of the open coil flat wire spring 101. When the angle 108 is decreased the torsional stiffness of the spring 101 is decreased and vice versa.

Figure 26:
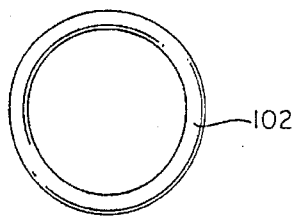
FIG. 26 shows the end view of the open coil flat wire spring shown in FIG. 25.

FIG. 26 shows the end view of the tubular blade.

Figure 27:
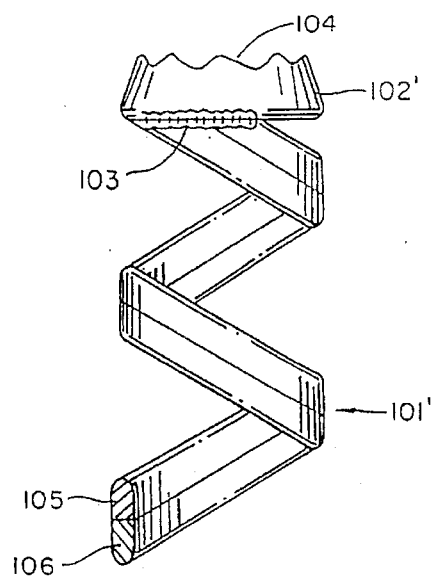
FIG. 27 shows a modified distal portion of the open coil flat wire spring in FIG. 24 where teeth are formed on the tubular cutting edge of the blade and the flat wire spring is constructed of two separate halves which makes it softer and easier to bend in order to follow the vessel's curves without substantially reducing its torque carrying capabilities.

FIG. 27 shows a modified distal portion of the open coil flat wire spring shown in FIGS. 24 to 26, where teeth 104 are formed on the cutting edge of the tubular blade 102' and the open coil flat wire spring 101' is constructed of two separate halves 105 and 106, to make it softer and easier for the open coil flat wire spring 101' to bend and follow the vessel's curves, but without substantially reducing its torsional stiffness and torque carrying capabilities.

The stent unclogging system can be manufactured in different diameters and lengths depending on the size and site of the vessel that it is intended for and whether the system is to be used percutaneously (which means gaining access to the vessel through the skin) or intra-operatively (that is when the vessel is surgically exposed for inserting the system into it). It can be noted from the figures that the basic components of the stent unclogging system can accept several optional features. The flexible rotary catheter can be made from plastic or metal. The coring means can vary. A regular guide wire can be used or a guide wire assembly having a helical wire or radial barrier means can be used. The sleeve can be equipped with mechanical or hydraulic biasing and flow blocking means.

By combining a certain flexible rotary catheter with a certain flexible casing (or with a flexible guide wire) and optionally adding a sleeve with or without biasing means, the characteristics of the system can be customized to treat individual patients. This is beneficial since the characteristics of obstructions in vessels and in stents vary widely in their length, their cross-sectional geometry, hardness, and in their location within the body.

FIGS. 28 through 31 show a variety of processes for unclogging an obstructed stent. One such process involves threading a flexible casing, preferably in the form of a helical wire 112 as illustrated in FIG. 29, through all of, or part of the length of, the obstruction material 115 clogging the stent. After threading the flexible casing into the obstruction the flexible casing is withdrawn to release and remove the material out of the stent, resulting in an unobstructed stent, as depicted in FIG. 31. Optionally, the flexible casing can be threaded part of the way through the length of the obstruction material and pulled to release this portion of the material. Then the helical wire can be threaded further into the material to release additional obstruction material, and pulled again to release additional material. This process can repeated as needed when dealing with longer obstructions. It should be noted that the above processes were not aided by the presence of a guide wire. To visualize these processes, FIG. 29 should be visualized with guide wire 113 absent from the drawings.

A variation of the process would involve inserting a flexible guide wire 113 into the obstructed stent, as illustrated in FIG. 28. A flexible casing, preferably in the form of a helical wire 112, is slid over and guided by the guide wire. The flexible casing is then threaded into the obstruction. The flexible casing is then withdrawn from the stent resulting in an unobstructed stent as depicted in FIG. 31.

Another variation of the process, particularly useful in cases where the obstruction material can not be readily pulled out of the stent, utilizes a tubular blade 117 attached to the distal end of the flexible rotary catheter 116. The process involves threading the flexible casing, preferably in the form of a helical wire 112, into the obstructed stent. A tubular blade 117 is then passed over the flexible casing and the obstruction material to separate the obstruction material from the stent. Then the flexible casing and the tubular blade are withdrawn from the stent resulting in an unobstructed stent as depicted in FIG. 31. It should be noted that the above process was not aided by the presence of a guide wire. To visualize this process, FIGS. 29 and 30 should be visualized with guide wire 113 absent from the drawings.

A further variation of the process comprises inserting a guide wire into the obstruction, as depicted in FIG. 28. The flexible casing, preferably in the form of a helical wire 112, is slid over and guided by the guide wire. The flexible casing is threaded into the obstruction. A tubular blade 117 is passed over the flexible casing and guide wire to separate the obstruction from the stent. Then the flexible casing and tubular blade are withdrawn from the stent resulting in an unobstructed stent as depicted in FIG. 31.

Additionally, FIG. 29 shows a preferred embodiment of the flexible casing in the form of a stainless steel continuous helical wire which has three sections: (i) a distal end section 114, (ii) a mid-section 118, and (iii) a proximal end 119 section. The three sections may have different winding pitches.

The distal end section 114 is closely wound relative to the helical wire's mid-section. The closely wound coils of the distal end define between them a void, thus facilitating the wire's engagement with the obstruction material. The proximal end section 119 is made of very close windings, relative to the mid-section, which can serve as a handle or as an area to which a handle can be affixed. The mid-section 118 is made of further spaced windings to connect the distal end section to the proximal end section.

The further spaced windings of the mid-section increase the torsional stiffness (compared to closer windings) of the mid-section, yet they are close enough to maintain the guide wire between the coils. Optionally, the mid-section or the proximal end section or both may be made of straight (uncoiled) wire.

The sequence of steps of the above discussed processes may vary depending on the nature and the location of the obstruction and the preferences of the medical staff. Furthermore, additional steps may be added to assist in the process. For example, a straight or curved standard guiding catheter, may be used as a sleeve and be placed into the vessel to assist in directing the system.

While the present invention has been illustrated by a limited number of examples, it should be understood that various modifications and substitutions may be made without departing from the spirit of the invention or the scope of the claims.

I claim:

1. A process for unclogging a stent that is located in a patient's vessel, comprising the following steps:

threading a helical wire into an obstruction material that is clogging the stent, and withdrawing the helical wire out of the stent.

2. A process as in claim I wherein said helical wire is slidable over a flexible guide wire.

3. A process as in claim 2 comprising the additional step:

inserting said flexible guide wire into the obstruction material.

4. A process for unclogging a stent that is located in a patient's vessel, comprising the following steps:

threading a helical wire into an obstruction material that is clogging the stent, passing a tubular blade over the helical wire and the obstruction material thereby separating the obstruction material from the stent, and withdrawing the helical wire and the tubular blade out of the stent.

5. A process as in claim 4 wherein said helical wire is slidable over a flexible guide wire.

* * * * *